(12) United States Patent
Johansen et al.

(10) Patent No.: US 6,592,867 B2
(45) Date of Patent: *Jul. 15, 2003

(54) ANTIMICROBIAL COMPOSITION CONTAINING AN OXIDOREDUCTASE AND AN ENHANCER OF THE N-HYDROXYANILIDE-TYPE

(75) Inventors: Charlotte Johansen, Holte (DK); Heinz-Josef Deussen, Soeborg (DK)

(73) Assignee: Novozymes A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/437,106

(22) Filed: Nov. 9, 1999

(65) Prior Publication Data

US 2002/0094331 A1 Jul. 18, 2002

Related U.S. Application Data

(60) Provisional application No. 60/108,651, filed on Nov. 16, 1998.

(30) Foreign Application Priority Data

Nov. 9, 1998 (DK) .......................... 1998 01441

(51) Int. Cl.[7] .......................... A61K 38/44; C12N 9/02; C12N 9/04; C12N 9/06; C12N 9/08
(52) U.S. Cl. ................. 424/94.4; 435/189; 435/190; 435/191; 435/192; 435/262
(58) Field of Search ................. 435/192, 191, 435/190, 189, 262; 424/94.4

(56) References Cited

U.S. PATENT DOCUMENTS

| 4,370,199 A | * | 1/1983 | Orndorff |
| 4,828,983 A | * | 5/1989 | McClune |
| 5,262,151 A | * | 11/1993 | Montgomery |
| 5,389,369 A | * | 2/1995 | Allen |
| 5,453,284 A | * | 9/1995 | Pellico |
| 5,700,769 A | * | 12/1997 | Schneider et al. |
| 5,801,226 A | * | 9/1998 | Cummins et al. |
| 5,866,393 A | * | 2/1999 | Fuglsang et al. |
| 5,948,661 A | * | 9/1999 | Sjoholm et al. |
| 6,069,282 A | * | 5/2000 | Fritz-Langhals et al. |

FOREIGN PATENT DOCUMENTS

| CA | 2212318 A | * | 2/1998 |
| EP | 0 825 294 A1 | | 2/1998 |
| WO | WO-9412620 A | * | 6/1994 |
| WO | WO 94/29425 | | 12/1994 |
| WO | WO-9527009 | * | 10/1995 |
| WO | WO-9527046 | * | 10/1995 |
| WO | WO 96/38548 | | 12/1996 |
| WO | WO 97/42825 | | 11/1997 |
| WO | WO 97/48786 | | 12/1997 |
| WO | WO 98/51772 | | 11/1998 |
| WO | WO 99/08531 | | 2/1999 |

* cited by examiner

*Primary Examiner*—Jon P. Weber
(74) *Attorney, Agent, or Firm*—Elias J. Lambiris

(57) ABSTRACT

The present invention relates to an enzymatic composition capable of killing or inhibiting microbial cells or microorganisms, e.g. in laundry, on hard surfaces, in water systems, on skin, on teeth or on mucous membranes. The present invention also relates to the use of said enzymatic composition for preserving food products, cosmetics, paints, coatings, etc.

16 Claims, 3 Drawing Sheets

ANTIMICROBIAL COMPOSITION CONTAINING AN OXIDOREDUCTASE AND AN ENHANCER OF THE N-HYDROXYANILIDE-TYPE

CROSS-REFERENCE TO RELATED APPLICATIONS

This application claims priority under 35 U.S.C. 119 of Danish application no. PA 1998 01441 filed on Nov. 9, 1998 and of U.S. application Ser. No. 60/108,651 filed Nov. 16, 1998, the contents of which are fully incorporated herein by reference.

FIELD OF THE INVENTION

The present invention relates to an enzymatic composition capable of killing or inhibiting microbial cells or microorganisms present, e.g., in laundry, on hard surfaces, in water systems, on skin, on teeth or on mucous membranes. The present invention also relates to the use of said enzymatic composition for preserving food products, cosmetics, paints, coatings, etc.

BACKGROUND OF THE INVENTION

Various enzymatic antimicrobial compositions are known in the art. For instance, WO 94/04127 discloses stabilized dentifrice compositions which are capable of producing antimicrobially effective concentrations of hypothiocyanite ions. The compositions contain an oxidoreductase capable of producing hydrogen peroxide and a peroxidase enzyme capable of oxidizing thiocyanate ions normally present in saliva to antimicrobial hypothiocyanite ions. Suitable peroxidases include lactoperoxidase, myeloperoxidase, salivary peroxidase and chloroperoxidase.

In EP-A-0 500 387 enzymatic antimicrobial compositions are disclosed comprising a haloperoxidase, e.g., myeloperoxidase, eosinophil oxidase, lactoperoxidase and chloroperoxidase, which selectively binds to and inhibits the growth of target micro-organisms in the presence of peroxide and halide.

WO 95/27046 discloses an antimicrobial composition comprising a Vanadium chloroperoxidase, halide ions, and hydrogen peroxide or a hydrogen peroxide-generating agent.

WO 96/38548 discloses an antimicrobial composition comprising a haloperoxidase, a halide ion, a peroxide generating agent and an amino acid.

WO 97/42825 discloses an antimicrobial composition comprising a peroxidase, a hydrogen peroxide source and an enhancing agent of the phenothiazine-type or of the acetosyringate-type.

The object of the present invention is to provide a composition for killing or inhibiting microbial cells.

SUMMARY OF THE INVENTION

According to the invention it has been found that an antimicrobial composition comprising a phenol oxidizing enzyme system and an enhancing agent comprising a —CO—NOH— group is very effective for killing or inhibiting microbial cells.

Thus, based on these findings, the present invention provides as a first aspect:

An enzymatic antimicrobial composition comprising a phenol oxidizing enzyme system and an enhancing agent of the following formula:

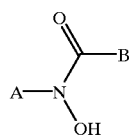

in which A and B independently of each other are:

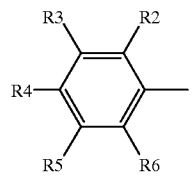

or B is H or $C_{1-16}$-alkyl, said alkyl may contain hydroxy, ether or ester groups, and R2, R3, R4, R5 and R6 independently of each other are H, OH, $NH_2$, COOH, $SO_3H$, $C_{1-12}$-alkyl, acyl, $NO_2$, CN, Cl, $CF_3$, NOH—CO-phenyl, CO—NOH-phenyl, $C_{1-6}$-CO—NOH—A, CO—NOH—A, COR12, phenyl-CO—NOH—A, OR7, NR8R9, COOR10, or NOH—CO—R11, wherein R7, R8, R9, R10, R11 and R12 are $C_{1-12}$-alkyl or acyl.

In further aspects, the present invention relates to methods for killing or inhibiting microbial cells, e.g. in laundry, in cosmetic products or on hard surfaces.

In still further aspects, the present invention relates to use of an enzymatic antimicrobial composition for cleaning of contact lenses, for cleaning of water systems, for preserving of paint, and in a cleaning-in-place system.

BRIEF DESCRIPTION OF DRAWINGS

The present invention is further illustrated by reference to the accompanying drawings, in which.

DETAILED DESCRIPTION OF THE INVENTION

Figure 1:
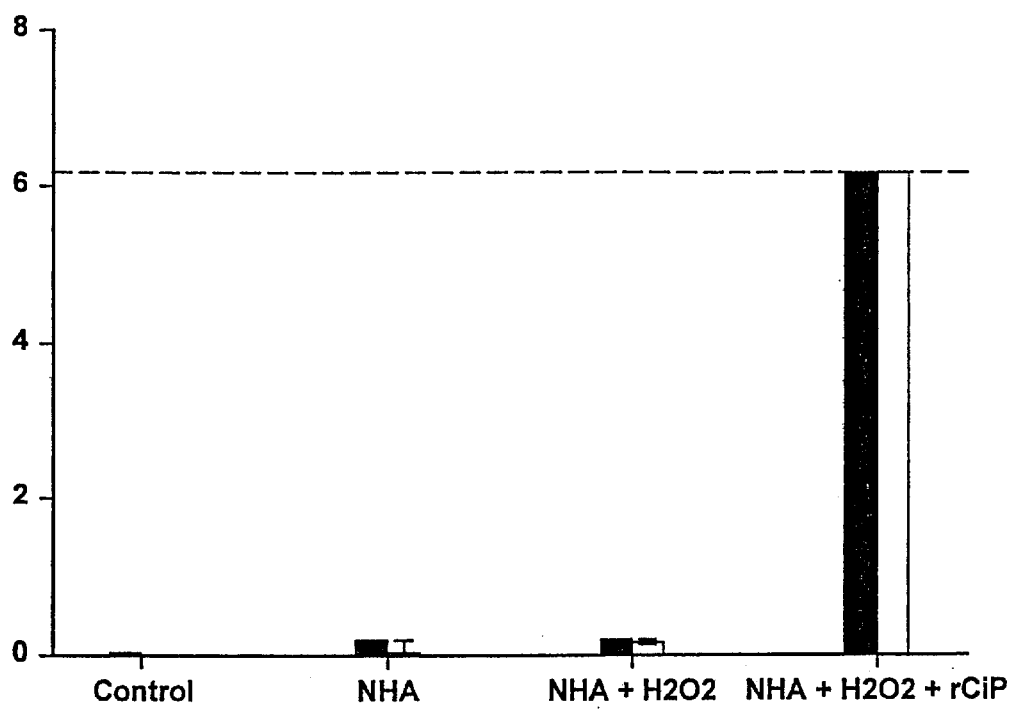
FIG. 1 shows the antimicrobial activity of C. cinereus peroxidase against P. fluorescens. (Peroxidase: 3 POXU/ml, Enhancing agent: 200 μM N-hydroxyacetanilide; see Example 1). ■=pH 8; □=pH 6; - - - -=total kill.

In the context of the present invention the term "antimicrobial" is intended to mean that there is a bactericidal and/or a bacteriostatic and/or fungicidal and/or fungistatic effect and/or a virucidal effect and/or a sporicidal effect, wherein The term "bactericidal" is to be understood as capable of killing bacterial cells.

Bactericidal activity is measured as a logarithmic reduction (log reduction) in the number of living cells or Colony Forming Units pr. ml (CFU/ml), e.g. 1 log reduction corresponds to a reduction in the number of living cells of

*Escherichia coli* DSM1576 or *Enterococcus faecalis* DSM2570 from $Y \times 10^X$ CFU/M (CFU: Colony Forming Units; M: ml or g) to $Y \times 10^{X-1}$ CFU/M, where X can be 1, 2, 3, 4, 5, 6, 7, 8, 9, 10 or 11, and Y can be any number from 0 to 10. The number of living cells are to be determined as the number of *E. coli* or *E. faecalis*, respectively, which can grow on Tryptone Soya Agar (#CM129, Oxoid, England) plates at 30° C.

The term "bacteriostatic" is to be understood as capable of inhibiting bacterial growth, i.e. inhibiting growing bacterial cells.

The term "fungicidal" is to be understood as capable of killing fungal cells.

The term "fungistatic" is to be understood as capable of inhibiting fungal growth, i.e. inhibiting growing fungal cells.

The term "virucidal" is to be understood as capable of inactivating virus.

The term "sporicidal" is to be understood as capable of inactivating spores.

The term "microbial cells" denotes bacterial or fungal cells, and the term "micro-organism" denotes a fungus (including yeasts) or a bacterium.

In the context of the present invention the term "inhibiting growth of microbial cells" is intended to mean that the cells are in the non-growing state, i.e., that they are not able to propagate.

The "phenol oxidizing enzyme system" describes an enzyme possessing peroxidase activity together with a hydrogen peroxide source, or a laccase or laccase related enzyme together with oxygen.

The term "hard surface" as used herein relates to any surface which is essentially non-permeable for micro-organisms. Examples of hard surfaces are surfaces made from metal, e.g., stainless steel, plastics, rubber, board, glass, wood, paper, textile, concrete, rock, marble, gypsum and ceramic materials which optionally may be coated, e.g., with paint, enamel and the like. The hard surface can also be a process equipment, e.g., a cooling tower, an osmotic membrane, a water treatment plant, a dairy, a food processing plant, a chemical or pharmaceutical process plant. Accordingly, the composition according to the present invention is useful in a conventional cleaning-in-place (C-I-P) system.

Enhancing Agents

The present invention relates to enhancing agents comprising a —CO—NOH— group of the following formula:

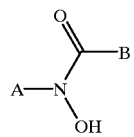

in which A and B independently of each other are:

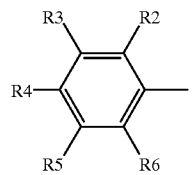

or B is H or $C_{1-16}$-alkyl, said alkyl may contain hydroxy, ester or ether groups (e.g. wherein the ether oxygen is directly attached to A—N(OH)C=O—, thus including N-hydroxy carbamic acid ester derivatives), and R2, R3, R4, R5 and R6 independently of each other are H, OH, NH$_2$, COOH, SO$_3$H, $C_{1-12}$-alkyl, acyl, NO$_2$, CN, Cl, Br, F, CF$_3$, NOH—CO-phenyl, CO—NOH-phenyl, $C_{1-6}$-CO—NOH—A, CO—NOH—A, COR12, phenyl-CO—NOH—A, OR7, NR8R9, COOR10, or NOH—CO—R11, wherein R7, R8, R9, R10, R11 and R12 are $C_{1-12}$-alkyl or acyl.

R2, R3, R4, R5 and R6 of A are preferably H, OH, NH$_2$, COOH, SO$_3$H, $C_{1-3}$-alkyl, acyl, NO$_2$, CN, Cl, Br, F, CF$_3$, NOH—CO-phenyl, CO—NOH-phenyl, COR12, OR7, NR8R9, COOR10, or NOH—CO-R11, wherein R7, R8 and R9 are $C_{1-3}$-alkyl or acyl, and R10, R11 and R12 are $C_{1-3}$-alkyl; more preferably R2, R3, R4, R5 and R6 of A are H, OH, NH$_2$, COOH, SO$_3$H, CH$_3$, acyl, NO$_2$, CN, Cl, Br, F, CF$_3$, CO—NOH-phenyl, COCH$_3$, OR7, NR8R9, or COOCH$_3$, wherein R7, R8 and R9 are CH$_3$ or COCH$_3$; even more preferably R2, R3, R4, R5 and R6 of A are H, OH, COOH, SO$_3$H, CH$_3$, acyl, NO$_2$, CN, Cl, Br, F, CO—NOH-phenyl, OCH$_3$, COCH$_3$, or COOCH$_3$; and in particular R2, R3, R4, R5 and R6 of A are H, OH, COOH, SO$_3$H, CH$_3$, NO$_2$, CN, Cl, Br, CO—NOH-phenyl, or OCH$_3$.

R2, R3, R4, R5 and R6 of B are preferably H, OH, NH$_2$, COOH, SO$_3$H, $C_{1-3}$-alkyl, acyl, NO$_2$, CN, Cl, Br, F, CF$_3$, NOH—CO-phenyl, CO—NOH-phenyl, COR12, OR7, NR8R9, COOR10, or NOH—CO—R11, wherein R7, R8 and R9 are $C_{1-3}$-alkyl or acyl, and R10, R11 and R12 are $C_{1-3}$-alkyl; more preferably R2, R3, R4, R5 and R6 of B are H, OH, NH$_2$, COOH, SO$_3$H, CH$_3$, acyl, NO$_2$, CN, Cl, Br, F, CF$_3$, CO—NOH-phenyl, COCH$_3$, OR7, NR8R9, or COOCH$_3$, wherein R7, R8 and R9 are CH$_3$ or COCH$_3$; even more preferably R2, R3, R4, R5 and R6 of B are H, OH, COOH, SO$_3$H, CH$_3$, acyl, NO$_2$, CN, Cl, Br, F, CO—NOH-phenyl, OCH$_3$, COCH$_3$, or COOCH$_3$; and in particular R2, R3, R4, R5 and R6 of B are H, OH, COOH, SO$_3$H, CH$_3$, NO$_2$, CN, Cl, Br, CO—NOH-phenyl, or OCH$_3$.

B is preferably H or $C_{1-3}$-alkyl, said alkyl may contain hydroxy, ester or ether groups; preferably said alkyl may contain ester or ether groups; more preferably said alkyl may contain ether groups.

In an embodiment, A and B independently of each other are:

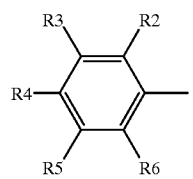

or B is H or $C_{1-3}$-alkyl, said alkyl may contain hydroxy, ester or ether groups (e.g. wherein the ether oxygen is directly attached to A—N(OH)C=O—, thus including N-hydroxy carbamic acid ester derivatives), and R2, R3, R4, R5 and R6 independently of each other are H, OH, NH$_2$, COOH, SO$_3$H, C$_{1-3}$-alkyl, acyl, NO$_2$, CN, Cl, Br, F, CF$_3$, NOH—CO-phenyl, CO—NOH-phenyl, COR12, OR7, NR8R9, COOR10, or NOH—CO-R11, wherein R7, R8 and R9 are C$_{1-3}$-alkyl or acyl, and R10, R11 and R12 are C$_{1-3}$-alkyl.

In another embodiment, A and B independently of each other are:

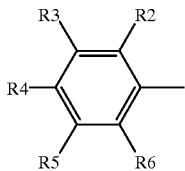

or B is H or C$_{1-3}$-alkyl, said alkyl may contain hydroxy or ether groups (e.g. wherein the ether oxygen is directly attached to A—N(OH)C=O—, thus including N-hydroxy carbamic acid ester derivatives), and R2, R3, R4, R5 and R6 independently of each other are H, OH, NH$_2$, COOH, SO$_3$H, CH$_3$, acyl, NO$_2$, CN, Cl, Br, F, CF$_3$, CO—NOH-phenyl, COCH$_3$, OR7, NR8R9, or COOCH$_3$, wherein R7, R8 and R9 are CH$_3$ or COCH$_3$.

In another embodiment, A and B independently of each other are:

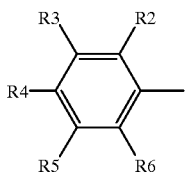

or B is H or C$_{1-3}$-alkyl, said alkyl may contain hydroxy or ether groups (e.g. wherein the ether oxygen is directly attached to A—N(OH)C=O—, thus including N-hydroxy carbamic acid ester derivatives), and R2, R3, R4, R5 and R6 independently of each other are H, OH, COOH, SO$_3$H, CH$_3$, acyl, NO$_2$, CN, Cl, Br, F, CO—NOH-phenyl, OCH$_3$, COCH$_3$, or COOCH$_3$.

In another embodiment, A and B independently of each other are:

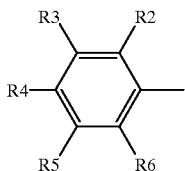

or B is C$_{1-3}$-alkyl, said alkyl may contain ether groups (e.g. wherein the ether oxygen is directly attached to A—N(OH)C=O—, thus including N-hydroxy carbamic acid ester derivatives), and R2, R3, R4, R5 and R6 independently of each other are H, OH, COOH, SO$_3$H, CH$_3$, NO$_2$, CN, Cl, Br, CO—NOH-phenyl, or OCH$_3$.

The terms "C$_{1-n}$-alkyl" wherein n can be from 2 through 16, as used herein, represent a branched or straight alkyl group having from one to the specified number of carbon atoms. Typical C$_{1-6}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl and the like.

The term "acyl" as used herein refers to a monovalent substituent comprising a C$_{1-6}$-alkyl group linked through a carbonyl group; such as e.g. acetyl, propionyl, butyryl, isobutyryl, pivaloyl, valeryl, and the like.

In an embodiment at least one of the substituents R2, R3, R4, R5 and R6 of A are H, preferably at least two of the substituents R2, R3, R4, R5 and R6 of A are H, more preferably at least three of the substituents R2, R3, R4, R5 and R6 of A are H, most preferably at least four of the substituents R2, R3, R4, R5 and R6 of A are H, in particular all of R2, R3, R4, R5 and R6 of A are H.

In another embodiment at least one of the substituents R2, R3, R4, R5 and R6 of B are H, preferably at least two of the substituents R2, R3, R4, R5 and R6 of B are H, more preferably at least three of the substituents R2, R3, R4, R5 and R6 of B are H, most preferably at least four of the substituents R2, R3, R4, R5 and R6 of B are H, in particular all of R2, R3, R4, R5 and R6 of B are H.

In particular embodiments according to the invention the enhancing agent is selected from the group consisting of 4-nitrobenzoic acid-N-hydroxyanilide;
4-methoxybenzoic acid-N-hydroxyanilide;
N,N'-dihydroxy-N,N'-diphenylterephthalamide;
decanoic acid-N-hydroxyanilide;
N-hydroxy-4-cyanoacetanilide;
N-hydroxy-4-acetylacetanilide;
N-hydroxy-4-hydroxyacetanilide;
N-hydroxy-3-(N'-hydroxyacetamide)acetanilide;
4-cyanobenzoic acid-N-hydroxyanilide;
N-hydroxy-4-nitroacetanilide;
N-hydroxyacetanilide;
N-hydroxy-N-phenyl-carbamic acid isopropyl ester;
N-hydroxy-N-phenyl-carbamic acid methyl ester;
N-hydroxy-N-phenyl-carbamic acid phenyl ester;
N-hydroxy-N-phenyl-carbamic acid ethyl ester; and
N-hydroxy-N-(4-cyanophenyl)-carbamic acid methyl ester.

The enhancing agent of the invention may be present in concentrations of from 1 to 1000 µM, preferably of from 5 to 500 µM, and more preferably from 10 to 200 µM.

Preparation of Enhancing Agents

The enhancing agents described in the present application may be prepared using methods well known to those skilled in the art; some of the enhancing agents are also commercially available.

The used compounds were prepared according to a general procedure described for N-hydroxyacetanilide (see Organic Syntheses 67, 1989, p. 187–192) followed by standard purification procedures.

Hydrogen Peroxide/Oxygen

If the phenol oxidizing enzyme requires a source of hydrogen peroxide, the source may be hydrogen peroxide or a hydrogen peroxide precursor for in situ production of hydrogen peroxide, e.g., percarbonate or perborate, or a hydrogen peroxide generating enzyme system, (e.g., an oxidase together with a substrate for the oxidase, e.g., an amino acid oxidase together with a suitable amino acid), or a peroxycarboxylic acid or a salt thereof. Hydrogen peroxide may be added at the beginning of or during the process, e.g., typically in an amount corresponding to levels of from 0.001–25 mM, preferably to levels of from 0.005–5 mM, and particularly to levels of from 0.01–1 mM.

If the phenol oxidizing enzyme requires molecular oxygen, molecular oxygen from the atmosphere will usually be present in sufficient quantity. If more O$_2$ is needed, additional oxygen may be added.

Phenol Oxidizing Enzyme

In the context of the present invention the enzyme of the phenol oxidizing enzyme may be an enzyme possessing peroxidase activity or a laccase or a laccase related enzyme.

The enzyme of the invention may typically be present in concentrations of from 1 to 10000 μg enzyme protein per liter aqueous solution, preferably of from 5 to 2000 μg enzyme protein per liter aqueous solution, more preferably of from 5 to 1000 μg enzyme protein per liter aqueous solution, and most preferably of from 1 to 500 μg enzyme protein per liter aqueous solution.

Peroxidases and Compounds Possessing Peroxidase Activity

Compounds possessing peroxidase activity may be any peroxidase enzyme comprised by the enzyme classification (EC 1.11.1.7), or any fragment derived therefrom, exhibiting peroxidase activity.

Preferably, the peroxidase according to the invention is producible by plants (e.g. horseradish or soybean peroxidase) or micro-organisms such as fungi or bacteria.

Some preferred fungi include strains belonging to the sub-division Deuteromycotina, class Hyphomycetes, e.g., Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens, Trichoderma resii, Myrothecium verrucaria* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes*.

Other preferred fungi include strains belonging to the subdivision Basidiomycotina, class Basidiomycetes, e.g., Coprinus, Phanerochaete, Coriolus or Trametes, in particular *Coprinus cinereus f. microsporus* (IFO 8371), *Coprinus macrorhizus, Phanerochaete chrysosporium* (e.g. NA-12) or Trametes (previously called Polyporus), e.g., *T. versicolor* (e.g. PR4 28-A).

Further preferred fungi include strains belonging to the subdivision Zygomycotina, class Mycoraceae, e.g., Rhizopus or Mucor, in particular *Mucor hiemalis*.

Some preferred bacteria include strains of the order Actinomycetales, e.g. *Streptomyces spheroides* (ATTC 23965), *Streptomyces thermoviolaceus* (IFO 12382) or *Streptoverticillum verticillium* ssp. *verticillium*.

Other preferred bacteria include *Rhodobacter sphaeroides, Rhodomonas palustri, Streptococcus lactis, Pseudomonas purrocinia* (ATCC 15958), *Pseudomonas fluorescens* (NRRL B-11) and Bacillus strains, e.g. *Bacillus pumilus* (ATCC 12905) and *Bacillus stearothermophilus*.

Further preferred bacteria include strains belonging to Myxococcus, e.g., *M. virescens*.

The peroxidase may furthermore be one which is producible by a method comprising cultivating a host cell transformed with a recombinant DNA vector which carries a DNA sequence encoding said peroxidase as well as DNA sequences encoding functions permitting the expression of the DNA sequence encoding the peroxidase, in a culture medium under conditions permitting the expression of the peroxidase and recovering the peroxidase from the culture.

Particularly, a recombinantly produced peroxidase is a peroxidase derived from a Coprinus sp., in particular *C. macrorhizus* or *C. cinereus* according to WO 92/16634.

In the context of this invention, compounds possessing peroxidase activity comprise peroxidase enzymes and peroxidase active fragments derived from cytochromes, haemoglobin or peroxidase enzymes.

Determination of Peroxidase Activity (POXU)

One peroxidase unit (POXU) is the amount of enzyme which under the following conditions catalyze the conversion of 1 μmole hydrogen peroxide per minute:

0.1 M phosphate buffer pH 7.0
0.88 mM hydrogen peroxide
1.67 mM 2,2'-azino-bis(3-ethylbenzothiazoline-6-sulfonate) (ABTS)
30° C.

The reaction is followed for 60 seconds (15 seconds after mixing) by the change in absorbance at 418 nm, which should be in the range 0.15 to 0.30.

For calculation of activity is used an absorption coefficient of oxidized ABTS of 36 $mM^{-1}$ $cm^{-1}$ and a stoichiometry of one μmole $H_2O_2$ converted per two μmole ABTS oxidized.

Laccases and Laccase Related Enzymes

In the context of this invention, laccases and laccase related enzymes comprise any laccase enzyme comprised by the enzyme classification (EC 1.10.3.2), any catechol oxidase enzyme comprised by the enzyme classification (EC 1.10.3.1), any bilirubin oxidase enzyme comprised by the enzyme classification (EC 1.3.3.5) or any monophenol monooxygenase enzyme comprised by the enzyme classification (EC 1.14.18.1).

The above mentioned enzymes may be microbial, i.e. derived from bacteria or fungi (including filamentous fungi and yeasts), or they may be derived from plants.

Suitable examples from fungi include a laccase derivable from a strain of Aspergillus, Neurospora, e.g., *N. crassa*, Podospora, Botrytis, Collybia, Fomes, Lentinus, Pleurotus, Trametes, e.g., *T. villosa* and *T. versicolor*, Rhizoctonia, e.g., *R. solani*, Coprinus, e.g., *C. cinereus, C. comatus, C. friesii*, and *C. plicatilis*, Psathyrella, e.g., *P. condelleana*, Panaeolus, e.g., *P. papilionaceus*, Myceliophthora, e.g., *M. thermophila*, Schytalidium, e.g., *S. thermophilum*, Polyporus, e.g., *P. pinsitus*, Pycnoporus, e.g. *P. cinnabarinus*, Phlebia, e.g., *P. radita* (WO 92/01046), or Coriolus, e.g., *C. hirsutus* (JP 2-238885).

Suitable examples from bacteria include a laccase derivable from a strain of Bacillus.

A laccase derived from Coprinus, Myceliophthora, Polyporus, Pycnoporus, Scytalidium or Rhizoctonia is preferred; in particular a laccase derived from *Coprinus cinereus, Myceliophthora thermophila, Polyporus pinsitus, Pycnoporus cinnabarinus, Scytalidium thermophilum* or *Rhizoctonia solani*.

The laccase or the laccase related enzyme may furthermore be one which is producible by a method comprising cultivating a host cell transformed with a recombinant DNA vector which carries a DNA sequence encoding said laccase as well as DNA sequences encoding functions permitting the expression of the DNA sequence encoding the laccase, in a culture medium under conditions permitting the expression of the laccase enzyme, and recovering the laccase from the culture.

Determination of Laccase Activity (LACU)

Laccase activity is determined from the oxidation of syringaldazin under aerobic conditions. The violet colour produced is photometered at 530 nm. The analytical conditions are 19 mM syringaldazin, 23 mM acetate buffer, pH 5.5, 30° C., 1 min. reaction time.

1 laccase unit (LACU) is the amount of enzyme that catalyses the conversion of 1.0 μmole syringaldazin per minute at these conditions.

Determination of Laccase Activity (LAMU)

Laccase activity is determined from the oxidation of syringaldazin under aerobic conditions. The violet colour produced is photometered at 530 nm. The analytical conditions are 19 mM syringaldazin, 23 mM Tris/maleate buffer, pH 7.5, 30° C., 1 min. reaction time.

1 laccase unit (LAMU) is the amount of enzyme that catalyses the conversion of 1.0 μmole syringaldazin per minute at these conditions.

The Composition

The antimicrobial composition according to the invention may be formulated as a solid or a liquid.

When formulated as a liquid, the composition is typically an aqueous composition.

When formulated as a solid, the composition is typically a powder, a granulate, a paste or a gelled product.

It is preferred to use a two part formulation system in the cases where hydrogen peroxide is needed, whereby the hydrogen peroxide is separate from the other components.

The composition of the invention may further comprise auxiliary agents such as wetting agents, thickening agents, buffer, stabilisers, perfume, colourants, fillers and the like.

Useful wetting agents are surfactants, i.e., non-ionic, anionic, amphoteric or zwitterionic surfactants.

The composition of the invention may be a concentrated product or a ready-to-use product. In use, the concentrated product is typically diluted with water to provide a medium having an effective antimicrobial activity, applied to the object to be disinfected or preserved, and allowed to react with the micro-organisms present.

The optimum pH of such an aqueous composition is usually a compromise between the optimum stability and optimum activity of the enzyme in question. In one aspect of the invention pH is in the range of pH 3 to 10.5, and in another aspect of the invention pH is in the range of pH 5 to 9.

The Method

The present invention also provides a method for killing or inhibiting microbial cells comprising treating said microbial cells with the composition of the invention. Said treatment may be carried out with an effective amount of said composition.

As an "effective amount" is meant an amount suitable for obtaining the required antimicrobial effect in the chosen application; e.g. to reduce the number of living cells to 10%, 1% or less than 1%; or to prevent the number of living cells from doubling during 12 hours, 1 day, 5 days, 30 days or more than 30 days.

Uses

The composition of the invention may be incorporated into a detergent or cleaning composition typically comprising other enzyme types as well (see below).

The composition of the invention can also be used for inhibiting micro-organisms present in laundry, by treating the laundry with a soaking, washing or rinsing liquor comprising an effective amount of the composition.

When used for preservation of paint, food, beverages, cosmetics such as lotions (e.g. eye lotions), liquids, creams, gels, pastes, ointments (e.g. eye ointments), soaps, shampoos, conditioners, antiperspirants, deodorants, mouth wash, nasal sprays, contact lens products, enzyme formulations, or food ingredients, the composition used in the method of the present invention may be incorporated into e.g. water based paint, unpreserved food, beverages, cosmetics, contact lens products, food ingredients or anti-inflammatory product in an amount effective for killing or inhibiting growth of microbial cells.

In particular, the composition of the invention may be used as a preservation agent or a disinfection agent in water based paints (see below).

Furthermore, the composition according to the present invention may by useful as a disinfectant, e.g., in the treatment of acne, infections in the eye or the mouth, skin infections; in antiperspirants or deodorants; in foot bath salts; for cleaning and disinfection of contact lenses, hard surfaces, teeth (oral care), wounds, bruises and the like.

In general the composition of the present invention is useful for cleaning, disinfecting or inhibiting microbial growth on any hard surface. Examples of surfaces, which may advantageously be contacted with the composition of the invention are surfaces of process equipment used, e.g., in dairies, chemical or pharmaceutical process plants, water sanitation systems, paper pulp processing plants, water treatment plants, and cooling towers. The composition of the invention may be used in an amount, which is effective for cleaning, disinfecting or inhibiting microbial growth on the surface in question.

In particular, the composition of the invention may be used for disinfecting and inhibiting microbial growth in paper and pulp processing plants.

Further, it is contemplated that the composition of the invention can advantageously be used in a cleaning-in-place (C.I.P.) system for cleaning of process equipment of any kind.

The method of the invention may additionally be used for cleaning surfaces and cooking utensils in food processing plants and in any area in which food is prepared or served such as hospitals, nursing homes, restaurants, especially fast food restaurants, delicatessens and the like. It may also be used as an antimicrobial in food products and would be especially useful as a surface antimicrobial for cheese, fruits and vegetables and for food in salad bars.

The composition of the present invention is also useful for microbial control of water lines, and for disinfection of water, in particular for disinfection of industrial water.

Conservation/Preservation of Paints

Conservation of paint products in cans has in the art been accomplished by adding non-enzymatic organic biocides to the paints. In the context of the invention paint is construed as a substance comprising a solid coloring matter dissolved or dispersed in a liquid vehicle such as water, organic solvent and/or oils, which when spread over a surface, dries to leave a thin colored, decorative and/or protective coating. Typically isothiazoliones, such as 5-chlor-2-methyl-4-thiazoli-3-on, has been added to the paint as biocides to inhibit/prevent microbial growth in the paint. The method of the invention can however suitably be applied in this field, thereby solving the problem of the ever present environmental bio-hazards of using toxic organic biocides by replacing these toxic biocides with environmentally compatible enzymes. Thus is the present invention provides a method for conservation of a paint comprising contacting said paint with a phenol oxidizing enzyme and an enhancing agent according to the invention. Further the invention provides a paint composition comprising a phenol oxidizing enzyme and an enhancing agent as described in the present invention.

The paint is preferably a water based paint, i.e. the solids of the paint is dispersed in an aqueous solution. The paint may contain 0–20% organic solvent, preferable 0–10%, e.g. 0–5%.

The enzyme may be added to the paint in an amount of 0.0001–100 mg active enzyme protein per liter paint, preferably 0.001–10 mg/l, e.g. 0.01–5 mg/l, while the enhancing agent may be added in an amount of 10–500 $\mu$M, preferably 25–250 $\mu$M, e.g. 100 $\mu$M of the paint composition.

Detergent Compositions

The antimicrobial composition of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the antimicrobial composition of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g. from *P. alcaligenes* or *P. pseudoalcaligenes* (EP 218 272), *P. cepacia* (EP 331 376), *P. stutzeri* (GB 1,372,034), *P. fluorescens*, Pseudomonas sp. strain SD 705 (WO 95/06720 and WO 96/27002), *P. wisconsinensis* (WO 96/12012), a Bacillus lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases ($\alpha$ and/or $\beta$) include those of bacterial or fungal origin. Chemically modified or protein engineered mutants are included. Amylases include, for example, $\alpha$-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from *C. cinereus*, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

The present invention is further illustrated in the following examples which are not in any way intended to limit the scope of the invention as claimed.

EXAMPLE 1

Antibacterial Activity of Coprinus Peroxidase with N-Hydroxyacetanilide as Electron Donor The antimicrobial activity of recombinant *Coprinus cinereus* peroxidase (rCiP), obtained as described in WO 92/16634, at pH 6 and pH 8 by use of N-hydroxyacetanilide as electron donor was tested.

Antimicrobial activity was evaluated in 0.05 M MES-buffer (Sigma M8250) (pH 6) or 0.05 HEPES-buffer (Sigma H3375) (pH 8); buffers were sterilised by filter sterilisation.

The antimicrobial activity was determined against *Pseudomonas fluorescens* (Gram et al. 1990, International Journal of Food Microbiology 10: 303–316) and *Staphylococcus epidermidis* (DSM 20042). Cells were grown in Tryptone Soya Broth (Oxoid CM129) at 30° C. (*S. epidermidis*) or 25° C. (*P. fluorescens*) for 24 h and diluted in the MES-buffer to a final cell concentration of approximately $10^6$ cfu/ml. The cell suspensions were mixed with rCiP (3 POXU/ml), enhancing agent (0.2 mM) and hydrogen peroxide (0.5 mM) for 20 min at 40° C. The bactericidal activity was determined by incubation in Malthus. Detection times measured by the Malthus instrument were converted to cfu/ml by a calibration curve. Either direct or Indirect Malthus measurements were used when enumerating total survival cells (Malthus Flexi M2060, Malthus Instrument Limited). By the direct measurements, the cell metabolism was determined by conductance measurements in the growth substrate. By the indirect measurements, 3 ml of growth medium was transferred to the outer chamber of the indirect Malthus cells, and 0.5 ml of sterile KOH (0.1 M) was transferred to the inner chamber. The cell suspensions were after enzyme treatment transferred to the outer chamber of the Malthus cell. As cells are growing in the outer chamber they produce $CO_2$ which will dissolve in the KOH in the inner chamber and thereby change the conductance of the KOH. The amount of $CO_2$ formed by the respiring cells surviving the enzyme treatment was used for estimating the number of viable cells. When the conductance change is measurable by the Malthus, a detection time (dt) will be recorded. The dt's were converted to colony counts by use of a calibration curve relating cfu/ml to dt (Johansen et al. 1995. Journal of Applied Bacteriology 78:297–303, Johansen et al. 1997, Applied and Environmental Microbiology 63:3724–3728).

No bactericidal activity of N-hydroxyacetanilide or N-hydroxyacetanilide combined with hydrogen peroxide was observed. Whereas a total kill was obtained by the combined system; N-hydroxyacetanilide, hydrogen peroxide and rCiP (see FIG. 1.). Gram-negative bacteria are in general most resistant towards combined oxidoreductase and enhancing agent systems. However, the total kill, corresponding to a cell reduction of approximately $10^6$ CFU/ml (Colony Forming Units), was obtained at both pH 6 and 8 (FIG. 1) against the Gram-negative bacterium P. fluorescens.

EXAMPLE 2

Bactericidal Activity of Laccases and N-Hydroxyacetanilide

Antibacterial activity of Polyporus pinsitus laccase (rPpL), obtained as described in WO 96/00290), and Coprinus cinereus laccase (rCcL), obtained as described in WO 97/08325, was determined with N-hydroxyacetanilide as enhancing agent against Pseudomonas aeruginosa (ATCC 10145), Enterobacter aerogenes (ATCC 13048) and Enterococcus faecalis (DSM 2570). The bactericidal activity was determined as described in Example 1, the antimicrobial activity of rPpL (1 mg/L) was evaluated at pH 6, whereas rCcL (1 mg/L) was evaluated at pH 8.

Figure 2:
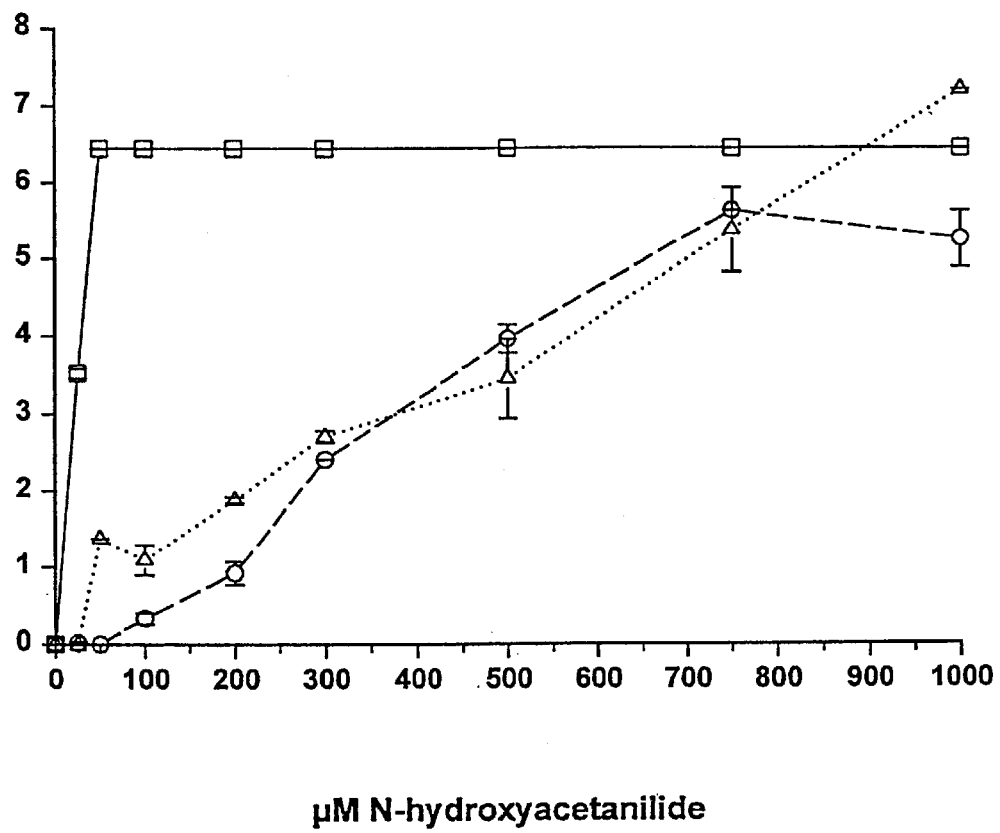
FIG. 2 shows the dosis-response curve for N-hydroxyacetanilide in combination with Polyporus laccase (rPpL) at pH 6, 20 min and 40° C. (see Example 2). —□—=Enterococcus faecalis; - -○- -=Pseudomonas aeruginosa; . . . Δ. . .=Enterobacter aerogenes.
Figure 3:
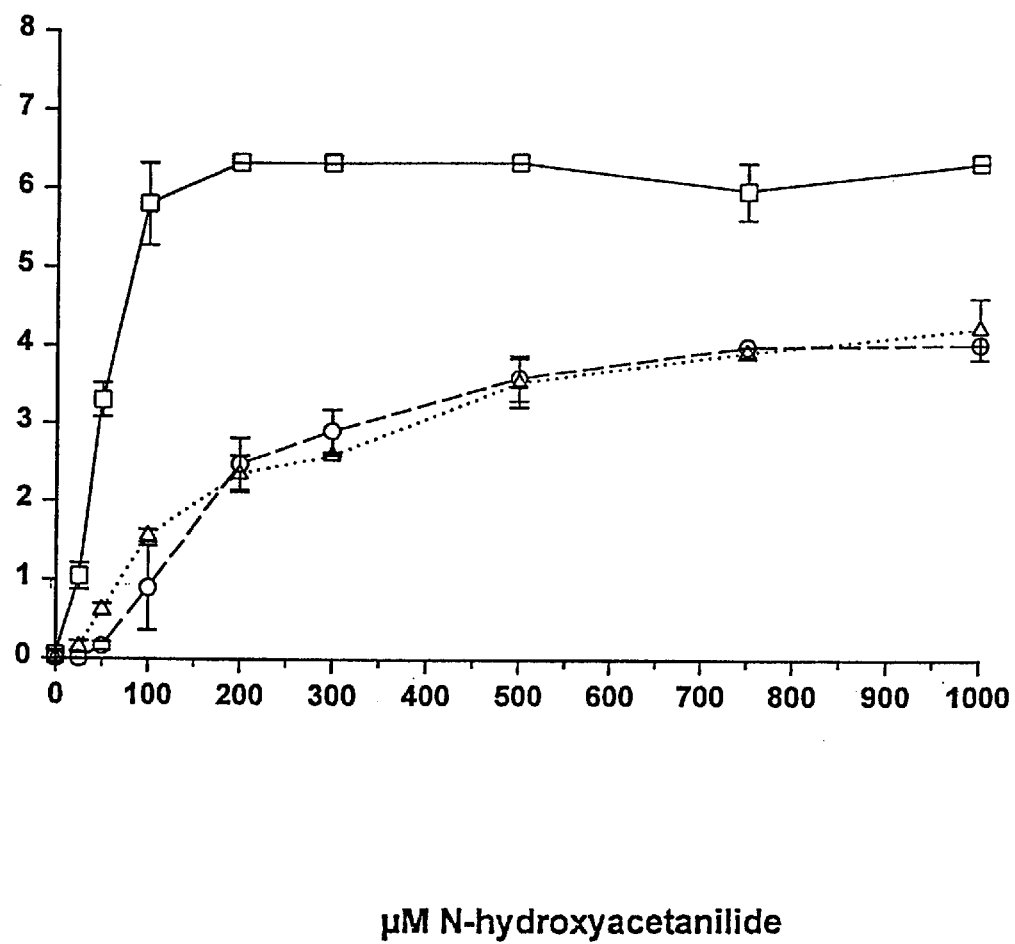
FIG. 3 shows the dosis-response curve for N-hydroxyacetanilide in combination with Coprinus laccase (rCcL) at pH 6, 20 min and 40° C. (see Example 2). —□—=Enterococcus faecalis; - -○- -=Pseudomonas aeruginosa; . . . Δ. . .=Enterobacter aerogenes.

Dose-Response curves for N-hydroxyacetanilide are shown when combined with rPpL (FIG. 2) or rCcL (FIG. 3).

A significant bactericidal activity was obtained against all the test organisms, with the Gram-negative strains being the most resistant. Bactericidal activity against P. aeruginosa ATCC 10145 was obtained at N-hydroxyacetanilide concentrations above 200 µM. When using the rPpL at pH 6, a total kill of the two gram-negative bacteria was obtained at high concentration of N-hydroxyacetanilide.

EXAMPLE 3

Bactericidal Activity of Various Phenol Oxidizing Enzymes and Enhancing Agents Antibacterial activity of Coprinus cinereus peroxidase (rCiP), Polyporus pinsitus laccase (rPpL), Coprinus cinereus laccase (rCcL) and Rhizoctonia solani laccase (rRsL) (as described in WO 95/07988) was determined with different enhancing agents at pH 6 and 8 (buffers; see Example 1). The rCiP was combined with 0.5 mM hydrogen peroxide.

Antimicrobial activity of rCiP and rPpL was determined against Pseudomonas fluorescens (Gram et al. 1990, International Journal of Food Microbiology 10:303–316), whereas antimicrobial activity of rCcL and rRsL was determined against Pseudomonas aeruginosa (ATCC 10145).

The bactericidal activity was determined as described in example 1. The different combinations and the results are shown in Table 1. The results are shown as the reduction in living cell number. Thus, a reduction of 4 correspond to a 4 log reduction of living cells e.g. from $10^6$ CFU/ml to $10^2$ CFU/ml.

TABLE 1

| | | Bactericidal activity | |
|---|---|---|---|
| Enzyme | Enhancing agent | Bactericidal activity (log CFU/ml) | pH |
| rCiP = 3 POXU/ml | N1-hydroxy-N1-phenyl-4-nitrobenzamide | 1.4 | 8 |

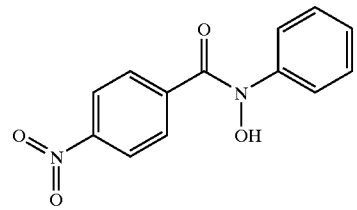

| rCiP = 3 POXU/ml | N1-hydroxy-N1-phenyl-4-methoxybenzamide | 4.1 | 6 |

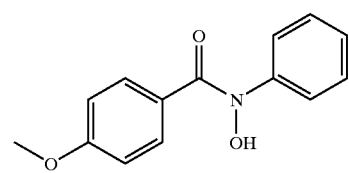

TABLE 1-continued

Bactericidal activity

| Enzyme | Enhancing agent | Bactericidal activity (log CFU/ml) | pH |
|---|---|---|---|
| rCiP = 3 POXU/ml | N1-(4-acetylphenyl)-N1-hydroxyacetamide | 1.2 | 6 |
| rCiP = 3 POXU/ml | N1-(4-hydroxyphenyl)-N1-hydroxyacetamide | 3.7 | 6 |
| rCiP = 3 POXU/ml | N1-(4-hydroxyphenyl)-N1-hydroxyacetamide | 1.1 | 8 |
| rCiP = 3 POXU/ml | N1-hydroxy-N1-phenyl-4-cyanobenzamide | 6.1 | 6 |
| rCiP = 3 POXU/ml | N1-hydroxy-N1-phenyl-4-cyanobenzamide | 2.1 | 8 |
| rCiP = 3 POXU/ml | N1-hydroxy-N1-(4-nitrophenyl)acetamide | 4.2 | 6 |

TABLE 1-continued

Bactericidal activity

| Enzyme | Enhancing agent | Bactericidal activity (log CFU/ml) | pH |
|---|---|---|---|
| rCiP = 3 POXU/ml | N1-hydroxy-N1-(4-nitrophenyl)acetamide | 1.2 | 8 |
| | 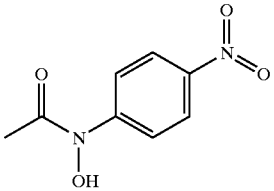 | | |
| rCiP = 3 POXU/ml | N1-hydroxy-N1-(3-nitrophenyl)acetamide | 1.5 | 6 |
| | 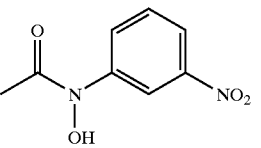 | | |
| rCiP = 3 POXU/ml | N1-hydroxy-N1-(3-nitrophenyl)acetamide | 1.1 | 8 |
| | 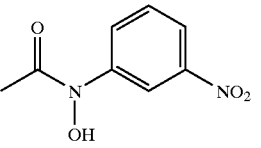 | | |
| rPpL = 5 mg/L | N1-hydroxy-N1-phenyl-4-methoxybenzamide | 4.8 | 8 |
| | 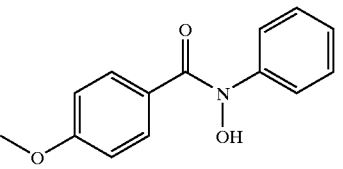 | | |
| rPpL = 5 mg/L | N1-(4-cyanophenyl)-N1-hydroxyacetamide | 1.7 | 6 |
| | 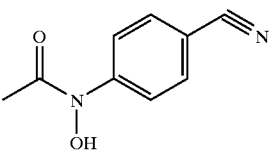 | | |
| rPpL = 5 mg/L | N1-hydroxy-N1-phenyl-4-cyanobenzamide | 2.5 | 6 |
| | 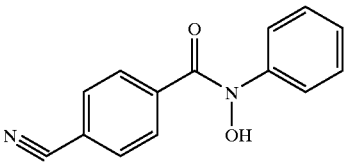 | | |

TABLE 1-continued

Bactericidal activity

| Enzyme | Enhancing agent | Bactericidal activity (log CFU/ml) | pH |
|---|---|---|---|
| rPpL = 5 mg/L | N1-hydroxy-N1-(4-nitrophenyl)acetamide 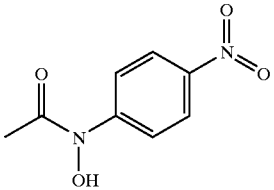 | 6.7 | 6 |
| rPpL = 5 mg/L | N1-hydroxy-N1-(4-nitrophenyl)acetamide 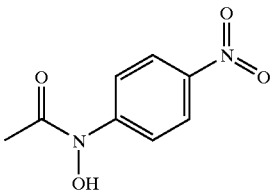 | 1.7 | 8 |
| rPpL = 5 mg/L | N1-hydroxy-N1-(3-nitrophenyl)acetamide 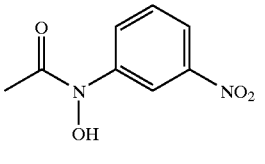 | 1.6 | 6 |
| rCcL = 5 mg/L | N1-hydroxy-N1-phenyl-4-methoxybenzamide 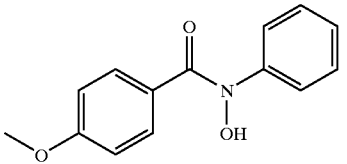 | 5.9 | 6 |
| rCcL = 5 mg/L | N1-hydroxy-N1-phenyl-4-methoxybenzamide 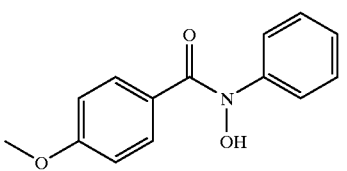 | 6.3 | 8 |
| rCcL = 5 mg/L | N1-hydroxy-N1-phenyl-4-cyanobenzamide 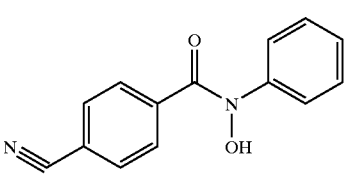 | 3.5 | 6 |

TABLE 1-continued

Bactericidal activity

| Enzyme | Enhancing agent | Bactericidal activity (log CFU/ml) | pH |
|---|---|---|---|
| rCcL = 5 mg/L | N1-hydroxy-N1-phenyl-4-cyanobenzamide | 6.5 | 8 |
| rRsL = 5 mg/L | N1-hydroxy-N1-phenyl-4-methoxybenzamide | 3.8 | 6 |
| rRsL = 5 mg/L | N1-hydroxy-N1-phenyl-4-methoxybenzamide | 4.6 | 8 |
| rRsL = 5 mg/L | N1-hydroxy-N1-phenyl-4-cyanobenzamide | 3.5 | 6 |
| rRsL = 5 mg/L | N1-hydroxy-N1-phenyl-4-cyanobenzamide | 6.5 | 8 |

EXAMPLE 4

Examples of Enhancing Agents

A) N1-hydroxy-N1-phenyl-4-nitrobenzamide, 4-nitrobenzoic acid-N-hydroxyanilide (CAS 2029-61-0);

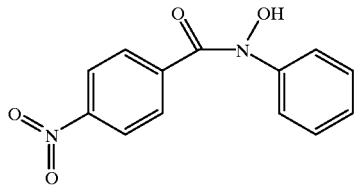

B) N1-hydroxy-N1-phenyl-4-methoxybenzamide, 4-methoxybenzoic acid-N-hydroxyanilide (CAS 13664-49-8);

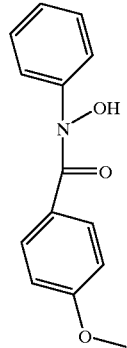

C) N,N'-dihydroxy-N,N'-diphenylterephthalamide (CAS 61494-26-6);

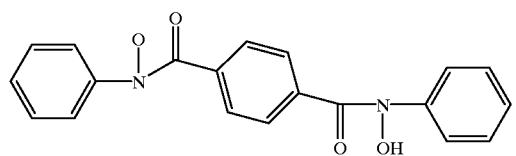

D) N1-(4-cyanophenyl)-N1-hydroxyacetamide, N-hydroxy-4-cyanoacetanilide (CAS 80584-65-2);

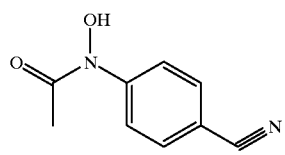

E) N1-hydroxy-N1-phenyldecaneamide, decanoic acid-N-hydroxyanilide (CAS 25310-16-1);

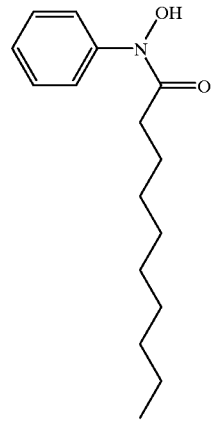

F) N1-hydroxy-N1-phenyl-4-cyanobenzamide, 4-cyanobenzoic acid-N-hydroxyanilide;

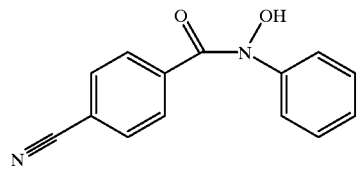

G) N1-(4-acetylphenyl)-N1-hydroxyacetamide, N-hydroxy-4-acetylacetanilide (CAS 67274-51-5);

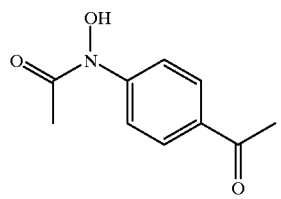

H) N1-hydroxy-N1-(3-nitrophenyl)acetamide;

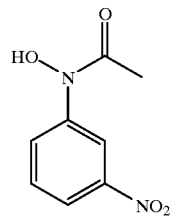

I) N1-(4-hydroxyphenyl)-N1-hydroxyacetamide, N-hydroxy-4-hydroxyacetanilide (CAS 63975-21-3);

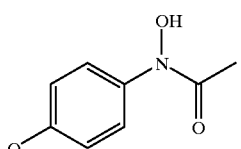

K) N1-hydroxy-N1-(4-nitrophenyl)acetamide, N-hydroxy-4-nitroacetanilide (CAS 67274-52-6);

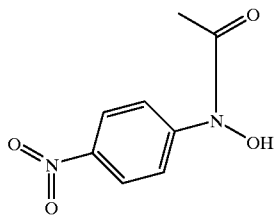

L) N-hydroxyacetanilide (CAS 1795-83-1);

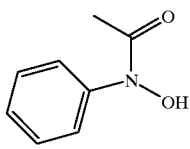

M) N-hydroxy-N-phenyl-carbamic acid isopropyl ester (CAS 4279-16-7);

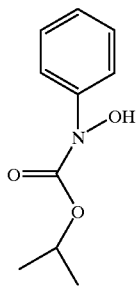

N) N-hydroxy-N-phenyl-carbamic acid methyl ester (CAS 28091-62-5);

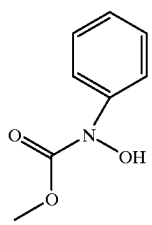

O) N-hydroxy-N-phenyl-carbamic acid phenyl ester (CAS 4645-72-1);

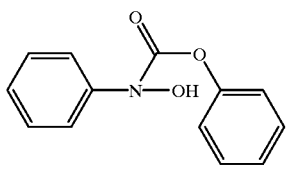

P) N-hydroxy-N-phenyl-carbamic acid ethyl ester (CAS 18631-99-7);

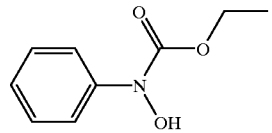

Q) N-hydroxy-N-(4-cyanophenyl)-carbamic acid methyl ester;

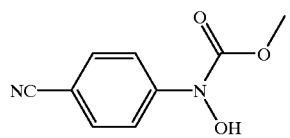

All compounds were synthesized according to a general procedure as outlined in Organic Syntheses 1989, 67, 187–192 for the synthesis of compound L). The procedure was modified concerning the work-up of the reaction mixtures and the purification of products. All structures were verified by their melting points from the literature, if available, and by $^1$H-NMR on VARIAN Mercury 400.

The following compounds have been described earlier:

A): S. Horner, Justus Liebigs Ann. Chem. 606, 1957, 24–28; O. Neunhoeffner, R. Gottschlich, Justus Liebigs Ann. Chem. 736, 1970, 100–109.
B): S. Horner, Justus Liebigs Ann. Chem. 606, 1957, 24–28; S. Jaimins, J. Indian Chem. Soc. 47, 1970, 247–249.
C): N. R. Gandhi, K. N. Munshi, J. Indian Chem. Soc. 59, 11112, 1982, 1290–1295; Munshi, K. N., Kharche, V. W., Junejai, H. D., Indian J. Chem. Sect. A, 27, 3, 1988, 222–224.
D): C. Poth Brink, A. C. Crumbliss, J. Org. Chem., 47, 7, 1982, 1171–1176.
E): Gupta; Tandon, J. Indian Chem. Soc., 46, 1969, 831–833.
G): C. Poth Brink, A. C. Crumbliss, J. Org. Chem., 47, 7, 1982, 1171–1176.
I): Healey; Calder, Aust. J. Chem., 32, 1979, 1307–1315; Gemborys, M. B. et al., J. Med. Chem., 21, 1978, 649–652.
K): Matlin, S. A. et al., J. Chem. Soc. Perkin Trans.1, 1979, 2481–2487.
M): Baskakow; Mel'nikow, Khim.Nauka Prom-st., 3, 1958, 683, Chem. Abstr., 1959, 7062; Patent, BASF-A.G., FR 1507608, 1967, Chem. Abstr., EN, 70, 57386e, 1969; Baskakow et al., Biol. Akt. Soedin.1968, 1968, 244–49.
N): Faddeewa; Baskakow, Biol. Akt. Soedin.1968, 1968, 199–06.
O): Oesper; Broker, J. Amer. Chem. Soc., 47, 1925, 2608; Baskakov et al., J. Org. Chem. USSR (Engl. Transl.), 3, 1967, 108, Zh. Org. Khim., 3, 1967, 112; Baskakow et al., J. Org. Chem. USSR (Engl. Transl.), 3, 1967, 108, Zh. Org. Khim., 3, 1967, 112.
P): Bamberger, Chem. Ber., 52, 1919–120; Journal, Tisue et al., Tetrahedron, 24, 1968, 999–004.

Synthesis of compounds F), H), and Q) are described below:

Synthesis of N1-Hydroxy-N1-Phenyl-4-Cyanobenzamide (F)

A solution of N-Phenylhydroxylamine (1.77 g, 16.2 mmol) in THF (30 ml) was synthesized as outlined in Org.

Synth. 1989, 67, 187–192. A slurry of sodium bicarbonate (2 g in 2 ml water) was added to the solution. The mixture was cooled to –2° C. and 4-cyanobenzoyl chloride (3.23 g, 19.51 mmol) was added dropwise. Stirring was continued overnight, before water (200 ml) was added. The reaction mixture was extracted 3× with methylene chloride. The solvent of the combined organic phases was removed in vacuo. The residue was purified chromatography using a Biotage Flash40i with SIM fitted with a 4.0×15.0 cm cartridge using AcOEt/Heptane (3:5, v:v) as eluting agent to give 0.55 g of pure f) (14%): mp: 146–147° C. $^1$H NMR (400 MHz, DMSO) d 10.93 (s, 1H), 7.93 (d, 2H), 7.80 (d, 2H), 7.62 (d, 2H), 7.42 (dd, 2H), 7.24 (t, 1H) . $^{13}$C NMR (100 MHz, DMSO) d 165.91, 140.82, 139.59, 131.45, 128.38, 128.11, 125.43, 121.30, 117.85, 111.99. Anal. Calculated for $C_{14}H_{10}N_2O_2$: C, 70.58; H, 4.23; N, 11.76 Found: C, 70.62; H, 4.32; N, 11.64.

Synthesis of N1-Hydroxy-N1-(3-Nitrophenyl) Acetamide (H)

Hydrazine hydrate (3.56 g, 71.11 mmol) was added dropwise to a suspension of 1,3-dinitrobenzene (6.0 g, 35.69 mmol) and wet 5% rhodium carbon (120 mg) in tetrahydrofuran (30 ml) keeping the temperature below 15° C. After stirring at room temperature overnight, the mixture is filtered and the catalyst washed with a little tetrahydrofuran. A slurry of sodium bicarbonate (6 g in 5 ml water) was added to the solution. The mixture was cooled to 0° C. and acetyl chloride (6.17 g, 78.60 mmol) was added dropwise. Stirring was continued overnight, followed by the addition of a solution of sodium hydroxide (5 g in 100 ml). The aqueous phase was separated, petroleum ether was added, and the tetrahydrofuran phase was separated again. The combined organic phases were extracted with aqueous 10% sodium hydroxide solution. The combined aqueous phases were washed with $CH_2Cl_2$ and then neutralized with hydrochloric acid. The mixture was extracted with $CH_2Cl_2$ and the extracts were combined, dried over magnesium sulphate, filtered and concentrated at reduced pressure. Upon the addition of petroleum ether, light orange crystals formed to give 4.59 g of pure (h) (66%): mp 92–94° C. $^1$H NMR (400 MHz, CDCl$_3$) d 9.41 (1H), 8.36 (1H), 7.96 (1H), 7.91 (1H), 7.46 (1H), 2.28 (3H). $^{13}$C NMR (100 MHz, CDCl$_3$) d 149.01, 130.52, 127.42, 121.25, 116.43, 23.45. Calculated for $C_8H_8N_2O_4$: C, 48.98; H, 4.11; N, 14.28 Found: C, 49.55; H, 4.16; N, 14.21.

Synthesis of N-Hydroxy-N-(4-Cyanophenyl)-Carbamic Acid Methyl Ester (O)

A solution of N-4-(cyanophenyl)hydroxylamine (3.13 g, 21.1 mmol) in THF (30 ml) was synthesized following the procedure described in Org. Synth. 1989, 67, 187–192 for the preparation of N-4-phenylhydroxylamine. A slurry of sodium bicarbonate (4.6 g in 7 ml water) was added to the solution. The mixture was cooled to –0° C. and methyl chloroformate (1.43 ml, 21.1 mmol) was added dropwise. Stirring was continued overnight before NaOH (8%, 30 ml) was added over 45 min. The water phase was separated. Petroleum ether (60 ml) was added to the THF-phase and the water phase was separated again. The organic phase was extracted 2× with 8% NaOH (40 ml). The combined water phases were washed with $CH_2Cl_2$ and neutralized with HCl (cooling!). The acidified water phase was extracted 3× with $CH_2Cl_2$ (60 ml). The combined organic phases were dried over $MgSO_4$, filtered, and the solvent was removed in vacuo to give crude (q). The compound was recrystallized from toluene/heptane to give 2.69 g of white crystals (66%): mp: 118–121° C. $^1$H NMR (400 MHz, CDCl$_3$) d 7.71 (d, 2H), 7.63 (d, 2H), 3.93 (s, 3H). $^{13}$C NMR (100 MHz, CDCl$_3$) d 154.16, 143.89, 132.52, 119.01, 118.54, 107.17, 54.22. Anal. Calculated for $C_9H_8N_2O_3$: C, 56.25; H, 4.20; N, 14.58. Found: C, 55.51; H, 4.24; N, 14.73.

What is claimed is:

1. A method for killing or inhibiting microbial cells, comprising treating the microbial cells with a composition comprising a laccase, oxygen, and an enhancing agent of formula (I):

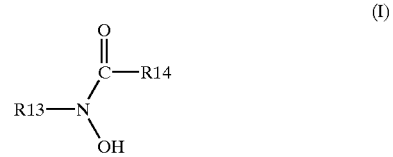

in which R13 and R14 independently are:

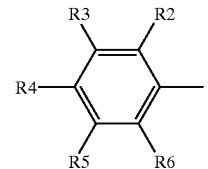

wherein R2, R3, R4, R5 and R6 independently are H, OH, $NH_2$, COOH, $SO_3H$, $C_{1-12}$-alkyl, acyl, $NO_2$, CN, Cl, Br, F, $CF_3$, NOH—CO-phenyl, CO—NOH-phenyl, $C_{1-6}$-CO—NOH—R15, CO—NOH—R15, COR12, phenyl-CO—NOH—R15, OR7, NR8R9, COOR10, or NOH—CO—R11, wherein R7, R8, R9, R10, R11 and R12 are $C_{1-12}$-alkyl or acyl, wherein R15 is

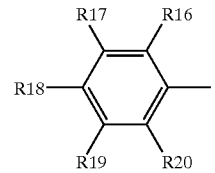

wherein R16, R17, R18, R19 and R20 independently are H, OH, $NH_2$, COOH, $SO_3H$, $C_{1-12}$-alkyl, acyl, $NO_2$, CN, Cl, Br, F, $CF_3$, NOH—CO-phenyl, CO—NOH-phenyl, $COR_{12}$, OR7, NR8R9, COOR10, or NOH—CO—R11, wherein R7, R8, R9, R10, R11 and R12 are $C_{1-12}$-alkyl or acyl.

2. The method of claim 1, in which R13 and R14 independently are:

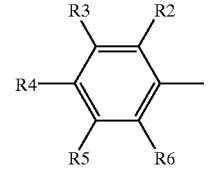

wherein R2, R3, R4, R5 and R6 independently are H, OH, COOH, $SO_3H$, $OH_3$, acyl, $NO_2$, CN, Cl, Br, F, CO—NOH-phenyl, $OCH_3$, $COOH_3$, or $COOCH_3$.

3. The method of claim 1, in which R13 and R14 independently are:

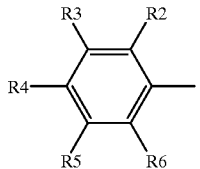

wherein R2, R3, R4, R5 and R6 independently are H, CH, COOH, $SO_3H$, $OH_3$, $NO_2$, CN, Cl, Br, CO—NOH-phenyl, or $OCH_3$.

4. The method of claim 1, in which the enhancing agent is selected from the group consisting of:
4-nitrobenzoic acid-N-hydroxyanilide;
4-methoxybenzoic acid-N-hydroxyanilide;
N,N'-dihydroxy-N,N'-diphenylterephthalamide;
N-hydroxy-3-(N'-hydroxyacetamide)acetanilide; and
4-cyanobenzoic acid-N-hydroxyanilide.

5. The method of claim 1, in which the laccase is a microbial laccase.

6. The method of claim 5, wherein the laccase is derived from Coprinus, Myceliophthora, Polyporus, Pycnoporus, Rhizoctonia, or Scytalidium.

7. The method of claim 6, wherein the laccase is derived from i Coprinus cinereus, Myceliophthora thermophila, Polyporus pinsitus, Pycnoporus cinnabarinus, Rhizoctonia solani, or *Scytalidium thermophilum*.

8. The method of claim 1, wherein the composition is an aqueous composition.

9. The method of claim 8, wherein the concentration of the laccase is in the range of from 0.001–10 mg enzyme protein per liter.

10. The method of claim 8, wherein the concentration of the enhancing agent corresponds to 1–1000 micro-M.

11. The method of claim 1, wherein the composition is a granulate.

12. A method of inhibiting microorganisms present in laundry, comprising treating the laundry with a soaking, washing or rinsing liquor comprising a composition comprising a phenol oxidizing enzyme system and an enhancing agent of the formula:

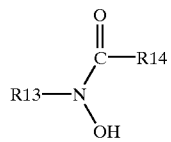

in which R13 and R14 independently are:

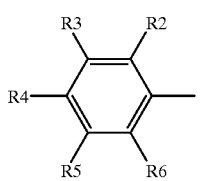

wherein R2, R3, R4, R5 and R6 independently are H, OH, $NH_2$, COOH, $SO_3H$, $C_{1-12}$-alkyl, acyl, $NO_2$, CN, Cl, Br, F, $CF_3$, NOH—CO-phenyl, CO—NOH-phenyl, $C_{1-6}$-CO—NOH—R15, CO—NOH—R15, COR12, phenyl-CO—NOH—R15, OR7, NR8R9, COOR10, or NOH—CO—R11, wherein R7, R8, R9, R10, R11 and R12 are $C_{1-12}$-alkyl or acyl, wherein R15 is

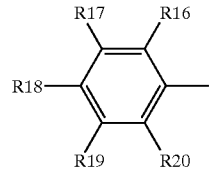

wherein R16, R17, R18, R19 and R20 independently are H, OH, $NH_2$, COOH, $SO_3H$, $C_{1-12}$-alkyl, acyl, $NO_2$, CN, Cl, Br, F, $CF_3$, NOH—CO-phenyl, CO—NOH-phenyl, COR12, OR7, NR8R9, COOR10, or NOH—CO—R11, wherein R7, R8, R9, R10, R11 and R12 are $C_{1-12}$-alkyl or acyl.

13. A method of cleaning, disinfecting or inhibiting microbial growth on a hard surface or contacting lenses, comprising contacting the surface or contact lenses with a composition comprising a phenol oxidizing enzyme system and an enhancing agent of the formula:

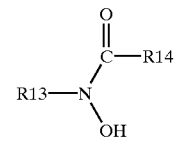

in which R13 and R14 independently are:

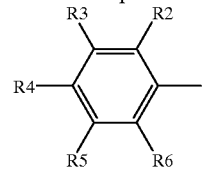

wherein R2, R3, R4, R5 and R6 independently are H, OH, $NH_2$, COOH, $SO_3H$, $C_{1-12}$-alkyl, acyl, $NO_2$, CN, Cl, Br, F, $CF_3$, NOH—CO-phenyl, CO—NOH-phenyl, $C_{1-6}$-CO—NOH—R15, CO—NOH—R15, COR12, phenyl-CO—NOH—R15, OR7, NR8R9, COOR10, or NOH—CO—R11, wherein R7, R8, R9, R10, R11 and R12 are $C_{1-12}$-alkyl or acyl, wherein R15 is

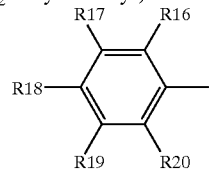

wherein R16, R17, R18, R19, and R20 independently are H, OH, $NH_2$, COOH, $SO_3H$, $C_{1-12}$-alkyl, acyl, $NO_2$, CN, Cl, Br, F, $CF_3$, NOH—CO-phenyl, CO—NOH-phenyl, COR12, OR7, NR8R9, COOR10, or NOH—CO—R11, wherein R7, R8, R9, R10, R11 and R12 are $C_{1-12}$-alkyl or acyl.

14. The method of claim 13, wherein the hard surface is a process equipment such as a member of a cooling tower, a water treatment plant, a dairy, a food processing plant, a chemical or pharmaceutical process plant.

15. the method of claim 13, wherein the hard surface is a surface of water sanitation equipment.

16. The of claim 13, wherein the hard sufface is a surface of equipment for paper pulp processing.

* * * * *